United States Patent [19]
Abrams et al.

[11] Patent Number: 6,117,066
[45] Date of Patent: *Sep. 12, 2000

[54] PREVENTION OF SEIZURE ARISING FROM MEDICAL MAGNETOICTAL NON-CONVULSIVE STIMULATION THERAPY

[75] Inventors: Richard Stephen Abrams, Chicago, Ill.; Conrad Melton Swartz, Richmond Heights, Mo.

[73] Assignee: Somatics, Inc., Lake Bluff, Ill.

[*] Notice: This patent is subject to a terminal disclaimer.

[21] Appl. No.: 09/159,045

[22] Filed: Sep. 23, 1998

Related U.S. Application Data

[63] Continuation-in-part of application No. 07/986,429, Dec. 4, 1992, abandoned, and a continuation-in-part of application No. 08/231,307, Apr. 22, 1994, Pat. No. 5,813,970.

[51] Int. Cl.$^7$ ............................................. A61N 1/00
[52] U.S. Cl. ........................................... 600/14; 128/897
[58] Field of Search .................... 600/9–15; 128/897–98; 607/45

[56] References Cited

U.S. PATENT DOCUMENTS

| | | | |
|---|---|---|---|
| 5,047,005 | 9/1991 | Cadwell | 600/14 |
| 5,116,304 | 5/1992 | Cadwell | 600/13 |
| 5,769,778 | 6/1998 | Abrams et al. | 600/14 |

*Primary Examiner*—John P. Lacyk
*Attorney, Agent, or Firm*—Eliot S. Gerber

[57] ABSTRACT

In non-convulsive magnetic stimulation therapy a patient is treated with magnetic pulses from a coil placed proximate the patient's head as a treatment of certain neurologic and psychiatric disorders. A set of EEG (electroencephalograph) electrodes on the patient's scalp are switched on during pauses in the electrical pulse train to the coil. If epilepsy-like brain wave spikes and/or sharp waves are detected by the EEG, a warning is given, treatment is halted and an anti-convulsive medicine may be administered.

20 Claims, 3 Drawing Sheets

PREVENTION OF SEIZURE ARISING FROM MEDICAL MAGNETOICTAL NON-CONVULSIVE STIMULATION THERAPY

RELATED APPLICATION

This application is a continuation-in-part based on applications Ser. No. 07/986,429, filed Dec. 4, 1992, now abandoned; and Ser. No. 08/231,307, filed Apr. 22, 1994, now U.S. Pat. No. 5,813,970.

FIELD OF THE INVENTION

The present invention relates to medical methods and more particularly to a system and method of preventing convulsive seizures of a patient undergoing magnetoictal non-convulsive stimulation therapy to treat certain neurologic and psychiatric disorders.

BACKGROUND OF THE INVENTION

The related art discloses various methods used in the past for inducing brain seizures in patients for the treatment of certain neurologic and psychiatric disorders ("neuropsychiatric disorders"), particularly certain types of psychotic depression. For example, brain seizures may be induced in human patients by the injection of chemical convulsant agents (pentylenetetiazol), the inhalation of gaseous convulsant agents (e.g. flurothyl), or by the application of electric currents to the scalp in a procedure termed electroconvulsive therapy (ECT), sometimes referred to as "shock therapy." Only ECT is still used to induce therapeutic brain seizures.

In addition, often various pharmacological agents (drugs) such as imipramine, lithium, bromazepam, etc. have been used to treat psychotic depression. However, sometimes such pharmacological agents have adverse side effects or are not effective.

In a present method of ECT, a pulsed or sinusoidal current of constant amperage or constant voltage is applied through electrodes to the patient's head for a period of 1–10 seconds. There are various possible drawbacks to ECT, however. These drawbacks include:

(1) The electrical resistance of the skull to the passage of current greatly attenuates the amount of current that actually reaches the brain. The rest of the current is shunted through the skin and scalp. Increasing the amount of current applied to the head, to reach the minimum required to induce seizures, may result in burns to the scalp and skin from the shunted current.

(2) Because the direct passage of electric current through the relatively high-impedance skin during ECT can cause skin burns, the doctor must reduce the impedance of the electrode-to-skin interface by first cleansing the skin, then wiping the skin dry, and applying conductive gel over the metal electrode surfaces and their application sites on the skin. Special effort is then required of the doctor to ensure that the metal disc electrodes are applied firmly to the skin, either by holding them in place with a rubber headstrap or holding them with manually applied non-conductive electrode handles. Alternatively, self-adherent, solid-gel disposable stimulus electrodes can be used, after first cleansing the skin and then wiping the skin dry. Metal disc electrodes, rubber headstraps, non-conductive electrode handles, and disposable self-adherent stimulus electrodes are all costly to purchase and time-consuming to maintain and use.

(3) The attenuated current that finally penetrates the skull is often capable only of stimulating seizures over the surface (cortex) of the brain. These seizures must then spread by secondary means to the deeper brain structures where the therapeutic effects of a seizure are believed to occur. Often these secondary means of spread are insufficient to induce therapeutic remission of the disorder.

(4) It has been reported that memory loss may accompany the passage of current through the temporal lobes of the brain.

(5) Leakage currents from defective equipment may reach the patient through the electrodes. Such leakage currents are dangerous to patients with cardiac arrhythmias or pacemakers. This requires that the ECT equipment undergo regular, and expensive, calibration checks.

(6) The negative stigma to much of the public to the phrase "shock therapy" causes many patients to refuse the treatment even though it would be beneficial to them.

(7) All convulsive therapies, including ECT, induce generalized brain seizures that stimulate superficial and deep subcortical brain structures indiscriminately. In some neuropsychiatric disorders, however, it is only the deep brain structures (e.g. the diencephalon) that functions abnormally and therefore requires stimulation.

(8) Generalized seizures have hemodynamic consequences (hypertension, tachycardia, increased intracranial pressure) that can present unacceptable risks to patients with pre-existing cerebral, cardiovascular, or cerebrovascular conditions (e.g. myocardial infarction, hypertension, stroke, brain tumor). These result from the spread of seizure activity into brain areas that control cardiovascular excitation, such as the medulla.

(9) Use of costly professional personnel and expensive facilities are usually required for ECT administration. Needed and billed services include anesthesiologist consultations and services, hospital pharmacy fees for solutions and anesthetics, and hospital fees for use of a treatment procedure room.

NCEST (non-convulsive electrical stimulation therapy) applies a pulsed current of constant low amperage or voltage. This stimulates surface and deep brain structure, but does not induce brain seizures because of the low energy used. When used at particularly low current it may act by direct stimulation of tissues only outside the central nervous system (CNS) and only indirect stimulation of the CNS. However, NCEST suffers from many of the drawbacks that appear in ECT and, in addition:

(1) The low energy current often fails to penetrate the bony skull in sufficient dosage to stimulate the deep subcortical brain structures that are believed to require the most stimulation. Any increase in the amount of current used increases the risk of the undesirable side-effects of generalized brain seizures that occur in ECT.

(2) The electric currents used in NCEST (and also in ECT) tend to diffuse through the brain as a volume conductor. This means the current is dispersed fairly evenly throughout the brain and cannot be focused, or concentrated, in a specific deep brain region, such as the diencephalon, to cause a therapeutic stimulation in just that region.

(3) Even the low energy currents used in NCEST may cause painful sensations in the skin and scalp that require the use of general anesthesia. The use of general anesthesia has been reported to cause mortality rates of approximately 0.001% due to gastric paresis with vomiting and aspiration pneumonitis, hypotensive cardiovascular collapse, or laryngospasm causing cerebral anoxia.

The inventor's prior U.S. Pat. No. 5,769,778 describes a method for stimulating surface, intermediate, or deep brain structures by the application of pulsed magnetic fields near the outside surface of the patient's head, e.g., transcranial magnetic stimulation therapy ("TMST"). The generated magnetic fields induce corresponding electrical fields in surface and deep brain structures, thereby depolarizing nerve cells and raising their level of excitation closer to the point of neuronal discharge. In the embodiment designated non-convulsive magnetic stimulation therapy (NCMST), the intended therapeutic agent is low-energy excitation of one or more brain structures without the induction of a generalized brain seizure.

Non-convulsive magnetic stimulation therapy (NCMST) has the following advantages compared to ECT:

1. It does not apply electric currents to the skin and so does not expose the subject to the risk of skin burns.
2. Its magnetic fields require no direct contact with the skin, so that time-consuming skin preparation is unnecessary and costly stimulus electrodes or accessories are not required.
3. There is no attenuation of the therapeutic stimulus before it reaches the deep brain structures because the bony skull does not significantly impede the transmission of magnetic fields. The intended strength electrical field current is directly induced in the brain region specified with NCMST.
4. Because magnetic fields can be oriented in three dimensions, to induce focused electrical field currents in deep brain structures, there is no necessity for the spread, and consequent attenuation, of brain tissue excitation from superficial to deep structures during the application of such magnetic fields.
5. It does not pass external electrical currents through the temporal lobes and consequently its use would not cause the same deleterious memory effects that have been reported in some cases from ECT.
6. It does not apply electric currents to the skin and, consequently, the patient receiving NCMST does not experience the painful electrical sensations or shocks possible with ECT. This avoids the need for general anesthesia which has morbid and mortal risks.
7. It requires no patient electrical or mechanical contact. The patient receiving NCMST is not subjected to the risks of leakage currents and there is no need for costly and time-consuming leakage current tests and impedance tests of the device.
8. No electrical stimuli or shocks are applied to the subject's head and the intent is not to induce a seizure. The method of NCMST is not "shock therapy", thus avoiding the prejudicial implications, to some members of the public, to this term.

Unfortunately, the application of NCMST may involve the risk, to the patient, of inducing a convulsive seizure, e.g. unplanned grand mal seizure. Individuals would be expected to differ in the amount of NCEST, i.e., the strength and duration of the magnetic fields, they could successively undergo without being thrown into seizure. Such a convulsive seizure may be frightening to the patient, and both physically and psychologically damaging to him. It may cause the patient to withdraw from further NCMST.

During the procedure of non-convulsive magnetic brain stimulation (NCMST) it is essential to avoid the induction of a seizure in the patient, especially because no muscle-relaxant drugs are given with NCMST (as they are with ECT). Such unmodified seizure induction may produce several noxious stresses, including cerebral hypoxia, cardiac ischemia, cyanosis, falling and other mechanical consequences of abrupt unconsciousness, elevation of intracranial pressure, two-fold elevation of cerebral blood flow, increase of blood pressure and heart rate, depletion of available metabolic energy by protracted seizure, and combination effects that exceed the sum of components such as neurotoxicity from simultaneous hypoxia and energy depletion. In addition, stresses from the muscular activity of unmodified grand mal seizures can lead to bone fractures, joint dislocations, aspiration pneumonitis, tooth fractures, tongue bites, and muscle sprains. Injuries can also result from seizure-induced confusion and disturbances of behavior. The risks of such injuries simply make unmodified grand mal seizures undesirable and their prevention a compelling priority.

One method to avoid convulsions, an adverse side effect, is to lower the stimulus dosage. But individuals, possibly because of gender, weight, age, physical condition, past brain injury history, and other factors, may widely differ in the amount of NCMST with which they can be treated, without convulsions. That amount of NCMST is presently not directly predictable and there is presently not even a data base of subjects treated with NCMST to arrive at a safe and yet effective amount. If the amount of NCMST is lowered to be perfectly safe (without causing convulsions) for all individuals, it is likely to be so low as to be ineffective for most patients.

There is presently no device or method which is commercially available to provide, on an individual-by-individual basis, the proper dosage of NCMST, i.e., a dosage which is sufficiently low to be safe (not induce seizure) and yet sufficiently high to be effective.

In U.S. Pat. No. 5,743,860 entitled "Apparatus And Method For Epileptic Seizure Detection Using Non-Linear Techniques," a patient's brain waves are analyzed using EEG (electroencephalograph) and chaotic time/series analysis to determine if a trend in non-linear measure indicates a seizure.

In U.S. Pat. No. 5,349,962 entitled "Method And Apparatus For Detecting Epileptic Seizures," an EEG and EMG (electromyograph) provide signals to signal processors. If either the EEG or EMG is above a window threshold it is an indication of seizure.

In U.S. Pat. No. 5,311,876, entitled "Automatic Detection Of Seizures Using Electroencephalographic Signals," a set of features contributing to discriminate seizure were selected.

The above-cited patents are incorporated by reference.

SUMMARY OF THE INVENTION

In NCMST a storage capacitor is discharged into a stimulating coil by means of one or more solid-state switches. The coil is positioned next to the head of the patient. The current in the coil generates a magnetic field pulse that induces a secondary current in the patient's brain tissue.

The voltage waveshape of the secondary current induced in the brain tissue is proportional to the rate of change of the magnetic field pulse. The delivered pulse, for example, may be a biphasic sine or square pulse with a duration of preferably 100 to 300 microseconds (usec). The pulse repetition rate is 1 Hz to 90 Hz and preferably about 1 to 20 Hz. The pulse train is preferably applied for about 1 to 10 minutes, most preferably for about 5 minutes. The primary coil current is in the preferred range of 2000–5000 A and the power is in the preferred range of 500–1500 watts. The magnetic flux density of the primary coil is preferably in the range of 1 to 5 Tesla, and most preferably about 2 Tesla.

The magnetic field produced by the magnetic induction coil is at least 0.1 Tesla and is preferably in the range of 0.5 to 2 Tesla.

The most preferred stimulus for non-convulsive magnetic stimulation therapy (NCMST) is a biphasic pulse train at a frequency of about 1 to 20 Hz (pulse width in the range of about 50–300 microseconds).

The patient is prevented from being over-stimulated and going into convulsions by monitoring the patient's on-going brain waves during NCMST using an electroencephalograph (EEG). If convulsions start, the NCMST is halted and the patient may optionally be medicated with anti-convulsive drugs.

The EEG system includes preferably at least two active scalp electrodes and most preferably four active scalp electrodes. The electrodes are arranged in symmetric pairs on opposite sides of the patient's scalp. In addition a reference electrode, at the mastoid, and a ground electrode are preferably used. The patient's brain waves are faint electrical signals at the microvolt level. It is not feasible to simultaneously measure EEG and provide NCMST, even using band-pass filters, because the pulsed magnetic coils generate electrical fields, which is overwhelming noise to the EEG.

To permit EEG during NCMST, the electrical pulse train to the magnetic coil (or coils) is interrupted on a programmed basis to provide "silent" periods (without NCMST), each preferably 1–10 seconds in duration. The EEG is switched on, by the system, only during these silent periods (non-NCMST). For example, in a 5 minute NCMST session, each minute has NCEST for 20 seconds, 5 seconds of silence (non-NCMST) and EEG, 20 seconds of NCMST, 5 seconds of silence and EEG, etc., etc.

It is preferred that a low frequency pulse train, i.e., 1–5 Hz, be used to activate the magnetic coil and that the EEG be switched on only between each pulse. It is sufficient to anticipate seizure, if the EEG is sampled at least twice each second, so that silent periods in a pulse train of 1–5 Hz are preferred.

The detection of the onset of convulsion is to detect spikes and/or sharp waves in the EEG. Such spikes and sharp waves are typical of the brain wave forms of epilepsy seizure detected by EEG. The spikes and sharp waves are preferably detected by an EEG system employing an amplifier, A/D (Analog/Digital) converter, computer and suitable software programming. In one embodiment spikes and sharp waves are defined by dV/dT (rise or fall in voltage over time) on both the front and back of the wave. Such spikes (and sharp wave forms) are also produced by artifact, particularly muscle artifact. Preferably, EEG spikes and sharp waves are automatically distinguished from artifact by the system on various bases. First, if spikes and/or sharp waves are simultaneously detected in all the EEG channels, it will be considered artifact. Secondly, an electromyograph (EMG) electrode is used to detect muscle movement. If both the EMG and EEG electrodes show simultaneous spikes (and/or sharp waves), it is considered an artifact. Thirdly, a convulsive spike or sharp wave is detected by a timed progression from one scalp area to another as the convulsive activity is propagated (spreads) across the brain. That progression occurs within a predetermined time period. Considering a pair of adjacent EEG channels, if the EEG shows a spike or sharp wave on one channel, the spike or sharp wave should also occur within a few milliseconds on the adjacent channel or it is considered an artifact and not convulsive activity.

Preferably, the EEG is analyzed on a time segment basis by the computer system; for example, each segment is 1–5 seconds long, preferably about 2 seconds long. The number of spikes/sharp waves in each segment is counted and if that counted number exceeds a predetermined number, i.e., 2–20 spikes, a warning is generated and stimulation is terminated.

Although spike and/or sharp wave detection is the preferred way to detect the onset of convulsions, it is also possible to have additional or alternative EEG measures including detection of an increase in coherence and the detection of a large voltage excursion. A large voltage excursion is considered a voltage rise by any point of the waveform from any EEG active electrode, i.e., 2.5 standard deviations (S.D.) above the RMS or average voltage level of a prior segment of 5 seconds from the same electrode.

In addition to the EEG electrodes, the system also has ECG (electrocardiograph) electrodes to monitor the patient's heart rate during NCMST. Preferably the R—R interval is monitored and if that individual R—R rate is increased it is considered an indication of the onset of seizure. For example, an R—R rate which is at least 40% faster than the patient's R—R rate prior to NCMST is considered such an indication of incipient seizure. In that event NCMST is halted and, optionally, the patient is treated with anti-convulsive drugs.

DETAILED DESCRIPTION OF THE INVENTION

Figure 1:
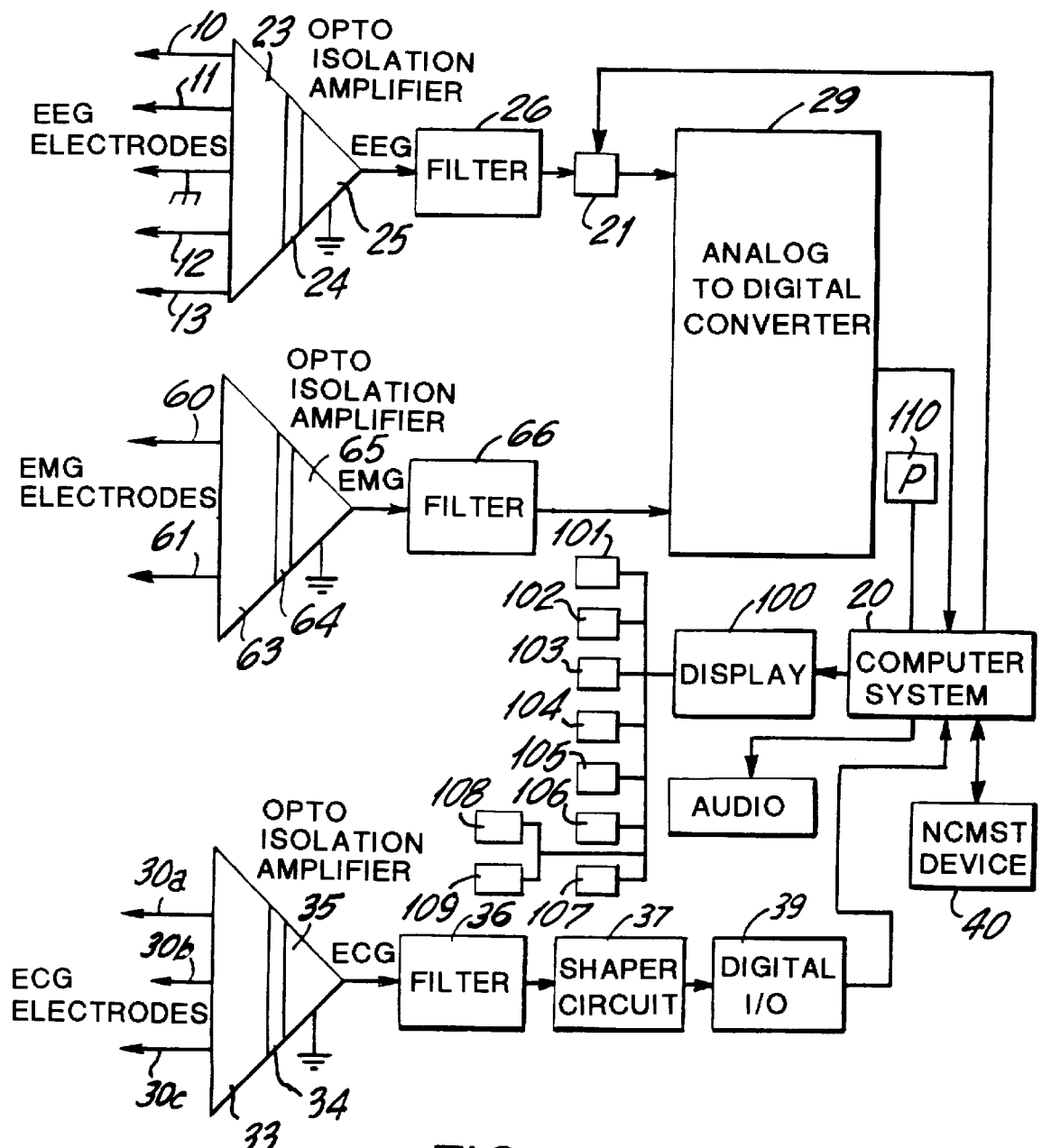
FIG. 1 is a schematic block diagram of the system of the present invention.

As shown in FIG. 1 the EEG (electroencephalograph) brain wave signal of the patient undergoing NCMST (Non-Convulsive Magnetic Stimulation Therapy) is determined from four disposable or reusable scalp electrodes 10–13 pasted on sites on the scalp. The electrodes 10,11 are on one side of the head and the electrodes 12,13 are on the opposite side of the head, forming two pairs 10,12 and 11,13 of active EEG electrodes. Alternatively, only two electrodes on opposite sides of the head may be used. The EEG signal is then amplified with differential instrumentation amplifier 23. To minimize unintended current exposure for patient safety, each signal is isolated with optoelectronic isolators 24. The EEG signal is then further amplified by amplifier 25 and its frequency is limited with a 2–25 Hz filter 26. The analog signal is then sampled and digitized by an analog-to-signal (A/D) converter 29, typically at 1000 samples per second.

The patient's brain waves, as detected by the EEG electrodes 10–13 and amplified and digitized by the EEG system, shown in FIG. 1, may be used to provide additional information to the operator. The EEG signal may be divided, by filters, into selected frequency bands within the 2–25 Hz band of filter 26. The Delta band is 2–3.5 Hz and, according to published studies, constitutes most of the brain wave energy generated during the induced seizure and is considered to be the seizure's primary component. The Theta band is 3.5–7.5 Hz, the Alpha band is 7.5–12.5 Hz and the lower portion of the Beta band is 12.5–25 Hz. Preferably the "absolute power" in the Delta band (2–3.5 Hz) is measured, although alternatively or in addition absolute power across the entire 2–25 Hz spectrum may be measured or absolute power in other bands may be measured.

Also, as shown in FIG. 1, the patient's muscle activity is considered an artifact and is detected by one, or more, EMG (electromyograph) electrodes 60,61 (two being shown).

The signals from electrodes 60 and 61 are amplified with a differential instrumentation amplifier 63. For patient safety the signal is isolated with optoelectronic isolator 64. The EMG signal is then further amplified by amplifier 65 and its frequency is limited with a 2–100 Hz filter 66. The analog signal is then sampled and digitized by the analog-digital (A/D) converter 29 at the millisecond rate (1000 samples/sec. channel) to provide digital data. The computer system 20, for example, using a 133 MHz "Pentium" processor (TM—Intel Corp.), is connected to A/D converter 29.

ECG signals are electrical potential traces or waves accompanied by the contraction of the different cavities of the heart. A typical ECG signal, produced by placing electrodes against the patient's skin, includes P, Q, R, S and T waves. These ECG signals are measured at frequencies of 0–50 Hz, this frequency range being normally sufficient for discerning such waves since the heartbeat rate is approximately 1 per second, and the rise time of these waves is in the order of 0.1 second.

Figure 2:
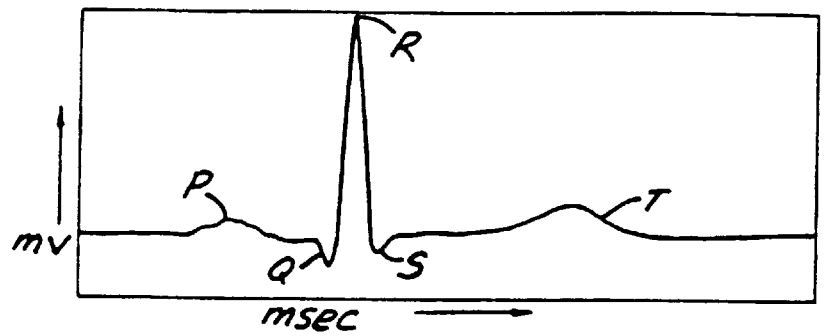
FIG. 2 is a diagram of a pulse train of electrical pulses to the coil.

A typical heart beat, as shown in FIG. 2, consists of an initial flat isoelectric portion; a "P" wave, a negative "Q" wave; an "R" wave whose leading-upward slope is the depolarization wave and whose lagging-downward slope is the repolarization wave; a negative "S" wave; the "S-T" segment between the S and T waves; the "T" wave, and sometimes a final small "U" wave. Preferably the heart rate is determined by the time interval between R wave peaks, although alternatively other portions of the heart waves may be detected and used to determine the rate. Preferably the heart beat rate is detected by at least 2 electrodes, plus one ground electrode, although the conventional 12-electrode system may be used.

In the embodiment shown in FIG. 1, the ECG signal (electrocardiograph), which detects heart activity, is sensed via two disposable or reusable electrodes 30a, 30b pasted on the chest of the patient, plus one ground electrode 30c. The ECG signal is amplified with a low-noise differential amplifier 33 (less than one microvolt of noise) having a band width of 0–300 Hz. For patient safety the signal is isolated with optoelectronic isolator 34. The ECG signal is then further amplified by amplifier 35 and its frequency is then limited with a 2–50 Hz filter 36. The signal is then passed through a shaper circuit 37 which detects the R-wave of the ECG and provides a square wave output compatible with detection by the digital circuitry of the computer system 20. The pulse output of shaper circuit 37 is connected to a digital input-output circuit 39 which provides a digital interrupt signal with every heartbeat, i.e., it is a rate detector. The heart rate is determined beat-to-beat by timing the interval between successive R waves. The system will calculate the time of the steepest drop in the heart rate. The pre-stimulus (baseline) frequency is determined over a 5-second period as a point of reference.

Figure 3:
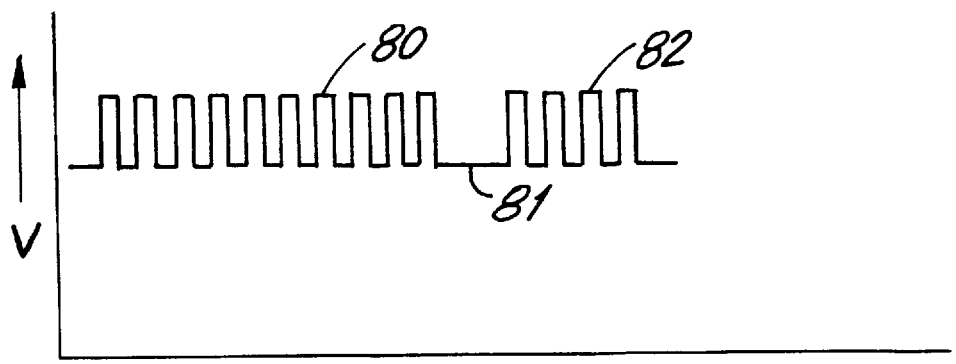
FIG. 3 is a circuit diagram of a magnetic stimulator.

The computer 20 of FIG. 1 is part of and controls the NCMST device 40 and its pulse generator, or alternatively the magnet stimulator circuit 50 may have its own microprocessor controller. The preferred electrical pulse train is shown in FIG. 3. It consists of a series of pulses 80, for example, 10 pulses during 30 seconds, followed by a silent period 81 of 1–10 seconds, preferably 2 seconds. This is repeated in pulses 82 and silent period, etc. The EEG is switched on, by solid-state switch 21, controlled by microprocessor computer system 20, only during the silent periods (non-NCMST periods). This avoids the noise from the coil from interfering with detection of the microvolt level brain signals by EEG.

Figure 4:
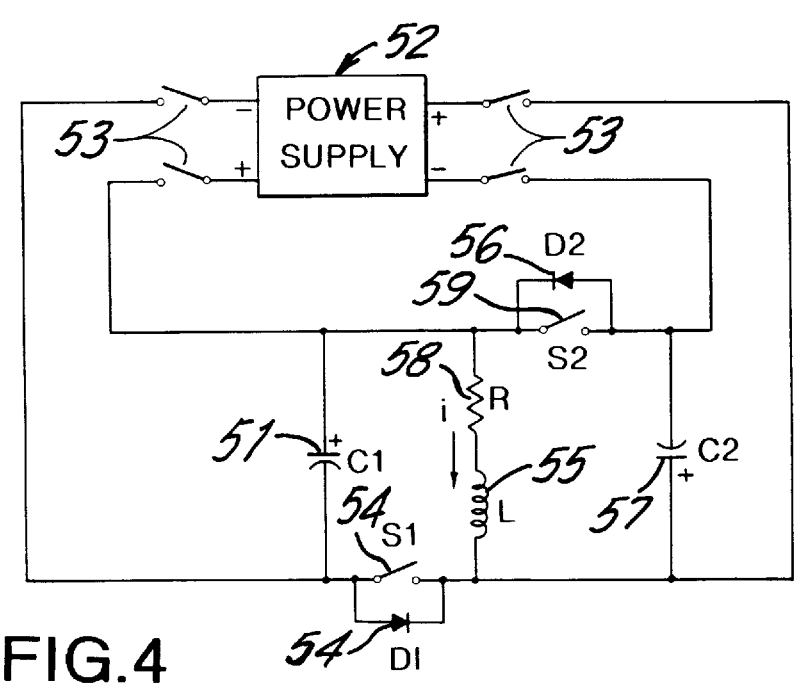
FIG. 4 illustrates the waveform of the current in the coil and the waveform of the voltage induced in the brain tissue.

The magnetic stimulator circuit 50 of FIG. 4, which is part of NCMST device 40, induces electrical currents in the living tissue of the brain of a human patient. Capacitor 51 (C1) is initially charged by a power supply 52 that is connected to capacitor 51 (C1) by solid-state switches 53. When capacitor 51 (C1) reaches a sufficient charge, these switches 53 open and the power supply 51 is disconnected from the circuit. Switch 54 (S1) is then closed, completing a circuit loop containing capacitor 51 (C1), switch 54 (S1), inductor coil 55 (L) and resistor 58 (R). Resistor 58 (R) represents the combined resistance of the cables, switches, capacitors, and coil L, and ideally is very low. The closing of switch 54 (S1) allows the charge on capacitor 51 (C1) to be discharged through the coil 55 (L). The current, i, in the coil 55 reaches its maximum when the voltage on capacitor 51 (C1) reaches zero. At that time, switch 54 (S1) is opened and the inductive force of coil 55 (L) turns on diode 56 (D2) and charges capacitor 57 (C2). Most of the initial charge on capacitor 51 (C1) will thus be transferred to capacitor 57 (C2) with relatively small losses due to the stimulation pulse. The power supply used to charge capacitor 51 (C1) is also switchable and is connected to capacitor 57 (C2) to "top off" capacitor 57 (C2). When capacitor 57 (C2) is fully charged, switch 59 (S2) closes and capacitor 57 (C2) discharges through the coil 55 (L) opening switch 59 (S2). When the voltage on capacitor 57 (C2) reaches zero inductor coil 55 (L) turns on diode 70 (D1) to "recharge" capacitor 51 (C1) and capacitor 57 (C2). The use of the inductive coil 55 (L) to recharge each capacitor 51 (C1) and 57 (C2) allows the capacitors to be recharged faster than using the power supply by itself. This allows for a higher pulse repetition rate. Having the coil 55 (L) discharge its inductive energy by charging the capacitor 51 (C1) and 57 (C2), whenever switches 54 (S1) and 59 (S2) are opened avoids having the coil 55 (L) dissipate the inductive energy as heat. This allows the device to have low heat dissipation and requires little, if any, external cooling.

Figure 5:
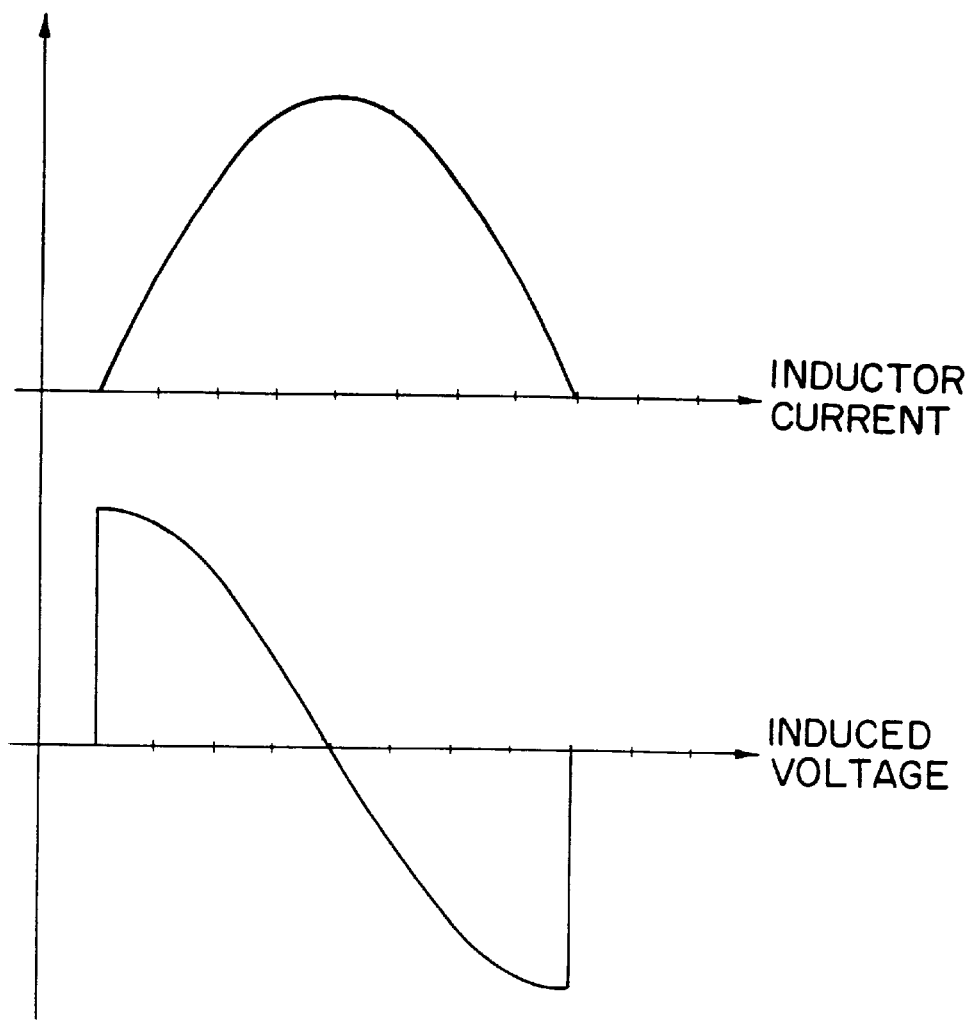
FIG. 5 is a top plan view of a magnetic stimulator portion of the system.

The inductor current, shown in FIG. 5, is proportional to the magnetic field induced by the coil 55 (L). This magnetic field generates an induced voltage in the brain tissue (also shown in FIG. 5) that is proportional to the rate of change (i.e., the first derivative) of the magnetic field. This results in the single monophasic cosine induced voltage pulse of FIG. 5.

The system may apply induced voltage pulses to selected focus points within the patient's brain. By proper selection of pulse repetition rate, amplitude and duration, therapeutic results in the treatment of neuropsychiatric disorders may be achieved. In nonconvulsive magnetic stimulation (NCMST), the intended therapeutic agent is low energy excitation of surface and deep brain structures without inducing a generalized brain seizure.

The strength of the magnetic field flux created by the coil 55 (L) will preferably be in the range of from 0.1 to 5 Tesla, and most preferably about 2 Tesla. For magnetic fluxes above 2.5 Tesla it may be necessary and more practical to use superconducting magnets to minimize the size of the coil and power requirements. The superconductor magnet may be of the type used in magnetic resonance imaging (MRI) systems in which a liquid helium cryostat is used to refrigerate a Low-Te superconductive magnet.

Figure 6:
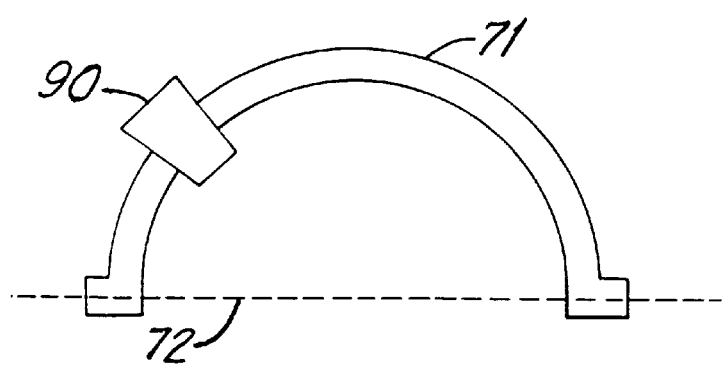
FIG. 6 is a front plan view of a display screen of the system of FIG. 1.

As shown in FIG. 6, the magnetic stimulation device may be housed in a Dewar container 90 that moves around the head on a semicircular track 71. The semicircular track 80 can then be pivotally mounted to allow the track to rotate about an imaginary axis 72 around the patient's head. This three-dimensional positioning of the coil and the variance of the strength of the induced voltage allow the operator to induce electrical currents at a particular focal point within the brain.

In the event a series of at least two spikes or sharp waves are detected by the EEG, or the heart rate detected by the ECG is above the danger level, the microprocessor 20 halts NCMST by a control signal to the pulse train generator, e.g., turns it off. In addition, a warning signal is given to the physician, for example, the warning signal is an audio buzzer or bell or the warning signal is a visual indication such as flashing words on a monitor or illuminating a sign. The physician may choose not to re-start NCMST until he determines if a seizure is about to commence. He may also choose to treat the patient using anti-convulsant drugs to avoid the oncoming seizure.

As shown in FIG. 1, the NCMST device 20 includes a number of visual displays 100 and a hard copy printer 110. The visual displays, including alphanumeric displays, which may be an LED (Light Emitting Diode) or a CRT (Cathode Ray Tube) monitor screen or an LCD (Liquid Crystal Display). Preferably it is built into the same housing as the NCMST device 20; but alternatively a separate monitor and printer may be used. The displays preferably include the EEG 101 (shown as wavy lines at each electrode); heart rate 102 (shown as a number); EEG amount of energy 103 in the high frequency range (10–50 Hz) (shown as a number); EEG coherence 104 as between left and right scalp) EEG electrodes (shown as a number); peak EEG amplitude 105 (shown as a number); EEG area 106 (the area under the curve of the absolute value of the EEG voltage (shown as a number); EEG area rate 107 (EEG area per unit time—shown as a number); maxima 108 and maxima 109 of the EEG area rate. The details of these EEG measures are found in the inventors U.S. Pat. No. 5,871,517 (application Ser. No. 08/784,128), as well as the inventors' prior U.S. Pat. Nos. 4,878,498; 4,873,891; 4,870,969; and 5,269,302, all incorporated by reference.

Preferably the printer 110 prints out a summary of treatment, at its conclusion, for record keeping purposes. The printed summary may include information as to the patient identification, type of stimuli, duration of stimuli, and all of the EEG and ECG numerical measurements. Such a record would be able to be analyzed to determine the amount/quality of the treatment and the absence/presence of seizure activity.

There is a reported interaction for TMS (TMST) between stimulus frequency and cortical stimulation site. Klein et al (Arch. Gen. Psych., in press) found a low-frequency (1 Hz) stimulus to the right prefrontal area to have significant antidepressant effects compared with sham TMS, an observation consistent with the report of Wasserman et al (Arch. Gen. Psych., in press) that low-frequency stimulation to the right prefrontal area induced localized hypometabolism, an effect also found with electroconvulsive therapy.

Pascual-Leone at al (1996) used a high-frequency (10 Hz) stimulus to treat patients assigned to one of several different stimulus sites, including the left prefrontal and right prefrontal areas; a sham rTMS group was included. Only high-frequency left prefrontal stimulation was significantly superior to sham rTMS.

The combined, simultaneous, application of low-frequency, right prefrontal stimulation and high-frequency left prefrontal stimulation has not been reported, yet the results should be summative—if not multiplicative—via a "push-pull" effect.

What is now disclosed is a method to simultaneously deliver low-frequency (e.g., in the range of 1–5 Hz) magnetic pulses to the right hemisphere, and high-frequency (e.g., in the range of 6–30 Hz) pulses to the left hemisphere, employing a device connected to two separate magnetic coils, utilizing a single power source. A single controller generates the pulse wave-form, and a single power driver sends the current to the magnetic coils via separate cables. An electronic switching device can be set to deliver the generated pulses to one or both hemispheres in the ratio desired. Thus, in one embodiment, a pulse frequency of 11 Hz is divided so that the first 10 pulses each second are directed to the left hemisphere and the 11th pulse is directed to the right hemisphere, resulting in a stimulus frequency of 1 Hz to the right hemisphere and 10 Hz to the left hemisphere.

Anti-convulsant drugs may be given prior to NCMST, particularly in the case of patients who have had a medical history of prior seizures.

Prevention of seizures is a similar concern after head injury, during hyperbaric oxygen therapy, and during high fevers in children. After head injury, administration of carbamazephine or phenytoin diminished the incidence of seizures (Schierhout et al 1998). In animal models, phenobarbital and carbamazepine, but not magnesium ion, prevented electrically induced seizures and phenytoin's efficacy varied between rats and cats (Standley et al 1949; Wada et al 1976). Similarly, vigabatrin (50–500 mg/kg) and carbamazepine (1.5–50 mg/kg), but not ethosuximide, prevented hyperoxia-induced seizure-like electrical discharges in the brain (Tzuk-Shina et al 1991; Reshef et al 1991). After the onset of febrile seizures, administration of phenobarbital or valproic acid diminished the incidence of further seizures (Rantala et al 1997). By analogy it is reasonable to expect that some anti-convulsant drugs will be more effective in the prevention of seizure during magnetic brain stimulation, i.e., carbamazepine and vigabatrin might be more effective than magnesium sulfate, ethosuximide, or phenytoin; nevertheless, even these agents might have some efficacy in some patients.

Although it is possible to wait for a warning before administering anti-convulsant drugs, it is preferable to administer one (or more) pharmaceutical agent(s) to the patient prior to the treatment, to diminish susceptibility to seizure and seizure-like activity. A variable aspect of the method is the means of administration and the selection of pharmaceutical agent(s). This method may be used alone, e.g., with or without the monitoring of physiologic EEG and ECG activity in the patient to detect the development of seizure during the treatment.

The pharmaceutical agent(s) can be administered through any of a variety of routes, including through mouth, rectal suppository, or parenteral injection, whether intramuscularly, intravenously, intraperitoneally, intrathecally, or subcutaneously. The pharmaceutical agent selected can be any medication identified to treat epileptic seizures, including those with such indication shown in the Physician's Desk Reference (PDR). Agents in this group include valproic acid, divalproex sodium, carbamazephine, phenytoin, primidone, vigabatrin, phenobarbital, topiramate, gabapentin, lamotrigine, and felbamate. Alternatively, the pharmaceutical agent selected can be any medication in the class of sedative-hypnotic agents, including barbiturates and benzodiazepines. Barbiturates include phenobarbital, amobarbital, secobarbital, methohexital, thiopental, and pentobarbital, among others. Benzodiazepines include diazepam, lorazepam, clonazepam, alprazolam, oxazepam, clorazepate, chlordiazepoxide, triazolam, and temazepam, among others. Alternatively, the pharmaceutical agent selected can be any anesthetic agent used for general narcosis which suppresses consciousness, whether injected or inhaled, including propofol, propanidid, fentanyl, althesin, thioamylal, and halothane gas. Typically, the patient will take orally 20–25 mg/Kg per day of valproic acid or 400 to 600 mg/day of carbamazepine for one to three days prior to treatment, or the patient will receive an intramuscular or intravenous injection of 100 to 400 mg of amobarbital or of secobarbital, or of 30 to 90 mg of phenobarbital.

If seizure-like or seizure-associated physiological activity is detected during magnetic brain stimulation, this will indicate to the operator that it is desirable to consider the addition of a pharmaceutical agent or a change in the pharmaceutical agent to diminish susceptibility to seizure. Some examples of seizure-like and seizure-associated physiological activity during the treatment are: increased EEG coherence, the development of or increase in sharp EEG activity, the appearance of spike-and-wave EEG activity, and the development of tachycardia. If the patient is already receiving a pharmaceutical agent to suppress seizure and seizure-like activity, the appearance of such physiological activity will suggest that it is desirable to increase the dose, to change to a different pharmaceutical agent with expected greater effectiveness, or to add another pharmaceutical agent to the present agent(s). This addition or change might be made during the same session or the same day, as by the parenteral injection of a barbiturate, or by the oral administration of carbamazepine or valproic acid. Alternatively, this addition or change might be made for use during a later session or later day.

What is claimed is:

1. A method to provide magnetic stimulation to the brain of a patient to treat neuropsychiatric disorders without inducing seizure in the patient comprising:
    (a) bringing a magnetic coil into proximity to the patient's head and pulsing the coil with electrical pulses to generate a sequence of magnetic fields within the patient's brain during a treatment session;
    (b) connecting an EEG (electroencephalograph) electrode to the patient's scalp to detect the patient's brain waves and detecting such brain waves during selected intervals during the treatment session;
    (c) detecting in the patient's brain waves the onset of epileptic spikes and/or sharp-waves and/or voltage excursions which are at least 2.5 standard deviations above RMS or average voltage level, and
    (d) providing a warning of such detection of the epileptic spikes and/or the sharp waves and/or the voltage excursions to halt the treatment session.

2. A method as in claim 1 and, in addition, after (d) treating the patient with a suitable anti-convulsant pharmaceutical agent.

3. A method as in claim 2 wherein the pharmaceutical agent is selected from the group consisting of: valproic acid, divalproex sodium, carbamazepine, phenytoin, primidone, vigabatrin, topiramate, gabapentin, lamotrigine, felbamate, phenobarbital, amobarbital, secobarbital, methohexital, pentobarbital, diazepam, lorazepam, clonazepam, alprazolam, oxazepam, midazolam, clorazepate, chlordiazepoxide, triazolam, nitrazepam, flurazepam, and temazepam, propofol, propanidid, fentanyl, althesin, thioamylal, and halothane gas.

4. A method as in claim 1 and switching the electrical pulses off and on to generate a series of off periods of at least 2 seconds and, in the treatment session, detecting the patient's brain waves only during such off periods.

5. A method as in claim 1 and removably attaching two ECG (electrocardiograph) electrodes to the patient, detecting the patient's heart rate, and providing a warning to halt the treatment session if the patient's heart rate rises above a selected rate.

6. A method as in claim 5 and deriving and displaying the patient's heart rate during the treatment session.

7. A method as in claim 1 and displaying an EEG based indication of the patient's condition during the treatment session, selected from one or more of the group of: (i) EEG displayed as wavy lines, (ii) amount of EEG energy in the high frequency range, (iii) EEG coherence, (iv) peak EEG amplitude, (v) EEG area, (vi) EEG area rate, and (v) maxima and minima of EEG area rate.

8. A method as in claim 1 and generating a summary report after the treatment session, the report being selected from one or more of the group of: (i) type of stimuli administered, (ii) number of stimuli administered, (iii) EEG measurements, and (iv) ECG measurements.

9. A method as in claim 1 and in (a) about simultaneously generating at least two sequences of magnetic fields; one sequence at one frequency on one side of the patient's brain and the other sequence at a different and higher frequency at the opposite side of the patient's brain.

10. A method as in claim 1 and in (c) counting the number of spikes and/or sharp waves in a time segment and, in the event the counted number exceeds a predetermined number, providing the warning of (d).

11. A system to provide magnetic stimulation to the brain of a patient for treatment of a neuropsychiatric disorder without inducing seizure in the patient comprising:
    (a) a magnetic coil adapted to be positioned in proximity to the patient's head and pulse means for pulsing the coil with electrical pulses to generate a sequence of magnetic fields that induce a sequence of electrical fields within the patient's brain during a treatment session;
    (b) an EEG (electroencephalograph) electrode adapted to be removably connected to the patient's scalp and EEG means to detect the patient's brain waves during selected intervals during the treatment session;
    (c) means for detecting in the patient's brain waves the onset of epileptic spikes and/or sharp-waves and/or voltage excursions which are at least 2.5 standard deviations above RMS or average voltage level, and
    (d) warning means for providing a warning to a physician of such detection of the epileptic spikes and/or the sharp-waves and/or the voltage excursions.

12. A system as in claim 11 and, in addition, means to warn a physician after (d) to treat the patient with a suitable anti-convulsive drug.

13. A system as in claim 11 and switch means for switching the electrical pulses off and on to thereby generate a series of off periods each of at least 2 seconds and, in the treatment session, means for detecting the patient's brain waves only during such off periods.

14. A system as in claim 11 and an ECG (electrocardiograph) electrode adapted to be removably connected to the patient, heart beat means for detecting the patient's heart rate, and heart beat warning means for providing a warning signal to a physician to halt the treatment session if the patient's heart rate rises above a selected rate.

15. A system as in claim 14 and means to calculate and display the patient's heart rate during the treatment session.

16. A system as in claim 11 and means to calculate and display an EEG based indication of the patient's condition during the treatment session, selected from one or more of the group of (i) EEG displayed as wavy lines, (ii) amount of EEG energy in the high frequency range, (iii) EEG coherence, (iv) peak EEG amplitude, (v) EEG area, (vi) EEG area rate and (vii) maxima and minima of the EEG area rate.

17. A system as in claim 11 and in (a) at least first and second magnetic coils positioned proximate opposite sides of the patient's head, and means to pulse the first coil with electrical pulses at a low frequency and to about simultaneously pulse the second coil with electrical pulses at a higher frequency.

18. A system as in claim 11 and in (c) means for counting the number of spikes and/or sharp waves in a time segment, comparing the counted number to a predetermined number and, in the event the counted number exceeds the predetermined number, generating a control signal to the warning means to provide the warning of (d).

19. A method of treatment of a patient for certain neurologic and psychiatric disorders, comprising in sequence:
(a) administering an anti-convulsive pharmaceutical agent to the patient and, when the patient has reacted to the anti-convulsive pharmaceutical agent;
(b) treating the patient with a series of magnetic impulses directed at the patient's head in a non-convulsive magnetic stimulation therapy session.

20. A method of treatment as in claim 19 wherein the pharmaceutical agent is selected from the group consisting of: valproic acid, divalproex sodium, carbamazepine, phenytoin, primidone, vigabatrin, topiramate, gabapentin, lamotrigine, felbamate, phenobarbital, amobarbital, secobarbital, methohexital, thiopental, diazepam, lorazepam, clonazepam, alprazolam, oxazepam, midazolam, clorazepate, chlordiazepoxide, triazolam, nitrazepam, flurazepam, halazepam, propofol, propanidid, fentanyl, althesin, thioamylal, and halothane gas.

* * * * *